(12) United States Patent
Court et al.

(10) Patent No.: US 6,268,544 B1
(45) Date of Patent: Jul. 31, 2001

(54) KNITTED WOUND DRESSINGS AND METHOD FOR MAKING SAME

(75) Inventors: Andrew D. Court, Little Neston; Peter M. J. Mahoney, Near Llanfyllin; Michael James Lydon, Mold, all of (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/194,929
(22) PCT Filed: Apr. 11, 1997
(86) PCT No.: PCT/EP97/01881
§ 371 Date: Apr. 13, 1999
§ 102(e) Date: Apr. 13, 1999
(87) PCT Pub. No.: WO98/46818
PCT Pub. Date: Oct. 22, 1998

(51) Int. Cl.$^7$ ................................................. A61F 13/00
(52) U.S. Cl. .................. 602/41; 602/42; 602/43; 602/44; 602/45; 602/46; 602/47
(58) Field of Search ................................... 602/41–47, 58

(56) References Cited

U.S. PATENT DOCUMENTS 4,920,203 * 4/1990 Tang et al. .
5,807,295 * 9/1998 Hutcheon et al. .

* cited by examiner

Primary Examiner—Michael A. Brown
Assistant Examiner—Lalita M. Hamilton
(74) Attorney, Agent, or Firm—Theodore R. Furman, Jr.; John M. Kilcoyne

(57) ABSTRACT

The present invention provides a wound dressing comprising a mixture of textile fibres and gel forming fibres wherein the dressing is a knitted fabric comprising support yarn and in-laid yarn, the support yarn being substantially free of gel-forming fibres.

14 Claims, 3 Drawing Sheets

KNITTED WOUND DRESSINGS AND METHOD FOR MAKING SAME

The invention relates to knitted wound dressings and particularly to wound dressings comprising a mixture of textile fibres and gel-forming fibres and a method for making same.

The invention also relates to a method of treating a wound comprising applying the dressing to a wound.

It is well known that the cleansing and debriding of wounds and the removal of wound exudate is important to the process of healing wounds. Commonly used wound dressings comprise gauze, foams, sponges, cotton wads or other fibrous materials. Gauze and other fibrous materials absorb fluids by capillary action with the disadvantage that when new tissue is formed as part of the healing process, it engulfs the fibres and is torn when the material is removed causing wound injury.

There thus exists a need for a dressing which is non-adherent while being absorbent.

PCT WO 95/91795 to Bristol-Myers Squibb Company describes a wound dressing comprising a mixture of textile fibres and gel-forming fibres to form an inexpensive, non-adherent dressing. The dressings disclosed are non-woven structures, the fibres being carded together to form a felt. Non woven fabrics generally have less tensile strength in both wet and dry states than woven fabrics. It is desirable for wound dressings to have a sufficiently high tensile strength that they may be handled during processing and packaging and be removable from a wound in a wet state, in one piece. For this reason woven fabrics are desirable as wound dressings. In addition a woven structure broadens the type of fibre that can be used in dressings.

In the past it has been difficult to produce knitted fabrics comprising gel-forming fibres because of the brittleness of the fibres. Their brittleness can lead to breakage and shedding of the gel-forming fibres during processing which not only limits machine speeds but is also undesirable in a product that is in direct contact with a wound.

We have now found that it is possible to make knitted wound dressings from a mixture of gel-forming fibres and textile fibres.

Accordingly the present invention provides a wound dressing comprising a mixture of textile fibres and gel-forming fibres wherein the dressing is a knitted fabric comprising support yarn and in-laid yarn, the support yarn being substantially free of gel-forming fibres.

The wound dressing according to the invention may have the advantage that fast knitting speeds are possible in the production of the dressing and the resulting product has better integrity than a dressing where gel-forming fibres are included in the support yarn.

The dressings may also have the advantage that because they are produced by knitting, the final product has good dimensional stability without the choice of fibre being unduly limited.

In the context of the present invention by yarn is meant a continuous strand of textile or staple fibers, filaments or other material in a form suitable for knitting. By staple yarn is meant a yarn composed of staple fibers held together by some binding mechanism such as twisting. By knitting is meant warp, weft or ring knitting.

Preferably the wound dressing is a warp knitted fabric. By warp knitting is meant a knit characterised by the fact that each warp yarn is more or less in line with the direction in which the fabric is produced. The warp yarn forms a support structure of pillars or chains of stitches and for this reason is also known as structural or pillar yarn. The pillars of stitches are held together by a further structural yarn and/or an in-laid yarn which is more or less perpendicular to the direction in which the fabric is produced. Examples of warp knitted fabrics are tricots, raschels, nets and laces such as are described in "Textile Science" by Kathryn L. Hatch, West Publishing Company 1993.

The knitted dressing preferably comprises from 5% to 95% of textile fibres by total weight of the dressing and from 5% to 95% of gel-forming fibres by total weight of the dressing. More preferably the dressing comprises from 15% to 70% by weight of gel-forming fibres and more particularly 20% to 60% by weight.

The textile fibres for use in the present invention can be natural or synthetic but are preferably cellulosic fibres for example viscose rayon, multi-limbed viscose, cotton, or regenerated cellulose or fibres having a higher absorbency than most textile fibres such as the multi-limbed cellulose fibres as described in EP-A-301874. In general textile fibres absorb liquids by capillary action and are not hygroscopic. This means that their absorbancies as measured by the free swell absorbancy test are low such as less than 1 gram of liquid per gram of fibre.

The gel-forming fibres for use in the present invention are hygroscopic fibres which upon the uptake of wound exudate become moist -and slippery or gelatinous and thus reduce the tendancy for the surrounding fibres to adhere to the wound. The gel-forming fibres may also swell and separate the textile fibres from the wound surface. The gel-forming fibres can be of the type which retain their structural integrity on absorption of exudate or can be of the type which lose their fibrous form and become a structureless gel or a solution on absorption of exudate.

The gel-forming fibres are preferably sodium carboxymethylcellulose fibres, chemically modified cellulosic fibres, in particular carboxymethylated cellulose fibres as described in PCT WO/9312275, pectin fibres, alginate fibres, fibres made from a composite of alginate and another polysaccharide, chitosan fibres, hyaluronic acid fibres, or other polysaccharide fibres or fibres derived from gums. In particular the alginate fibres described in EP-A-0721355 to Bristol-Myers Squibb Company are particularly preferred. The cellulosic fibres preferably have a degree of substitution of at least 0.05 carboxymethyl groups per glucose unit. The gel-forming fibres preferably have an absorbency of at least 2 grams 0.9% saline solution per gram of fibre (as measured by the free swell absorbency test) and a tenacity of at least 10 cN/tex. The production of solvent-spun cellulose fibres is described for example in U.S. Pat. No. 4,246,221 and U.S. Pat. No. 4,196,281 as well as in PCT WO/9312275. The gel-forming fibres for use in dressings of the present invention may also be composite or co-spun gel-forming fibres as described in our co-pending applications GB9607600.5 and GB9618658.0 which describe fibres that are composites of alginate and another polysaccharide or those described in PCT WO 96/10106 to Innovative Technologies Limited.

Preferably the gel-forming fibres for use in the present invention have an absorbency of at least 15 g/g as measured in the free swell absorbency method, more preferably between 25 g/g and 50 g/g.

The gel-forming fibres suitable for use in the present invention can be processed using conventional textile machinery, for example by the staple route including cutting, carding and if desired crimping,. drafting and spinning.

The wound dressing of the present invention may be made by spinning or twisting gel-forming fibres and textile fibres together to form the in-laid yarn and then warp knitting using a yarn consisting of textile fibres as the pillar yarn to form a gauze, bandage or stocking. The wound dressing of the present invention may be used as a primary or secondary dressing especially in the treatment of leg ulcers.

The in-laid yarn may be a staple yarn comprising from 0% to 80% by weight of textile fibre and 20% to 100% of gel-forming fibre, more preferably from 0% to 75% by weight of textile fibre and 25% to 100% of gel-forming fibre. Alternatively the in-laid yarn may be a continuous filament yarn comprising from 20% to 100% of gel-forming fibres.

The support yarn is preferably a continuous filament viscose, polypropylene, polyester, polyamide or polyethylene yarn or mixture thereof.

The wound dressing of the invention preferably comprises from 5% to 80% by weight of support yarn and from 20% to 95% by weight of in-laid yarn. More preferably from 5% to 60% of support yarn and from 40% to 95% of in-laid yarn.

Various optional ingredients can also be included in the final composition such as preservatives and small amounts of pharmacologically active ingredients. For example an antibiotic or antimicrobial agent such as metronidazole, silver sulphadiazine, neomycin or penicillin and antiseptic agent such as povidone iodine and antiinflammatory agent such as hydrocortisone or triamcinolone acteonide or a skin protective agent such as a zinc oxide can be included.

These ingredients can be added to the fibres during production or coated on the fibres, screen printed or spray coated on the dressing.

Preferred embodiments of the invention are illustrated in the accompanying drawings in which.

Figure 1:
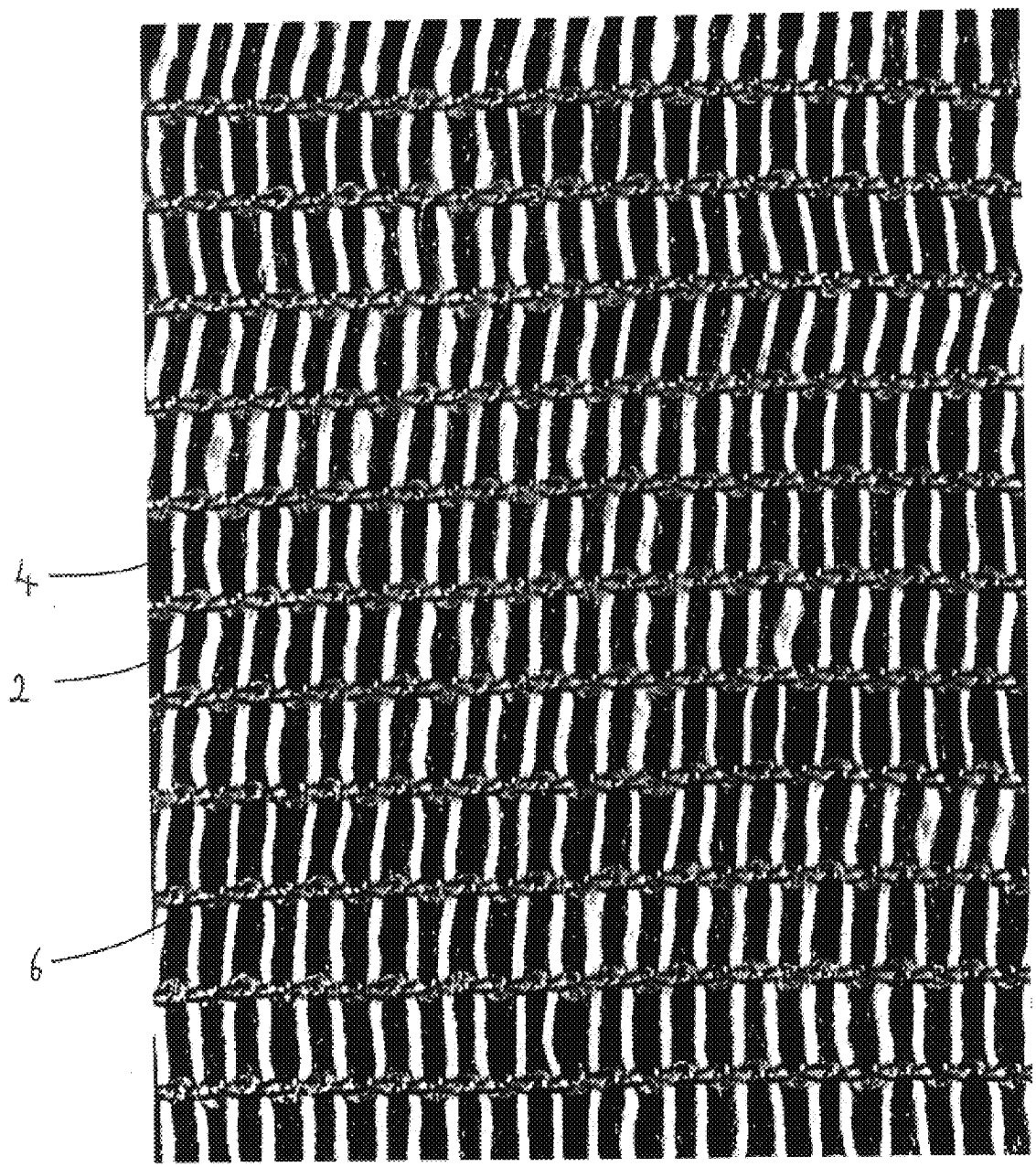
FIG. 1 is a photograph on an enlarged scale of a first embodiment of a wound dressing according to the invention.

FIG. 1 shows a wound dressing according to the invention where the dressing is a knitted fabric comprising support yarn 2) and in-laid yarn (4), the support yarn (2) being substantially free of gel-forming fibres. The knitted fabric is a warp knitted fabric meaning that each warp yarn (6) is more or less in line with the direction in which the fabric was produced. The warp yarn (6) is in the form of pillars or chains of stiches held together by the in-laid yarn (4).

Figure 2:
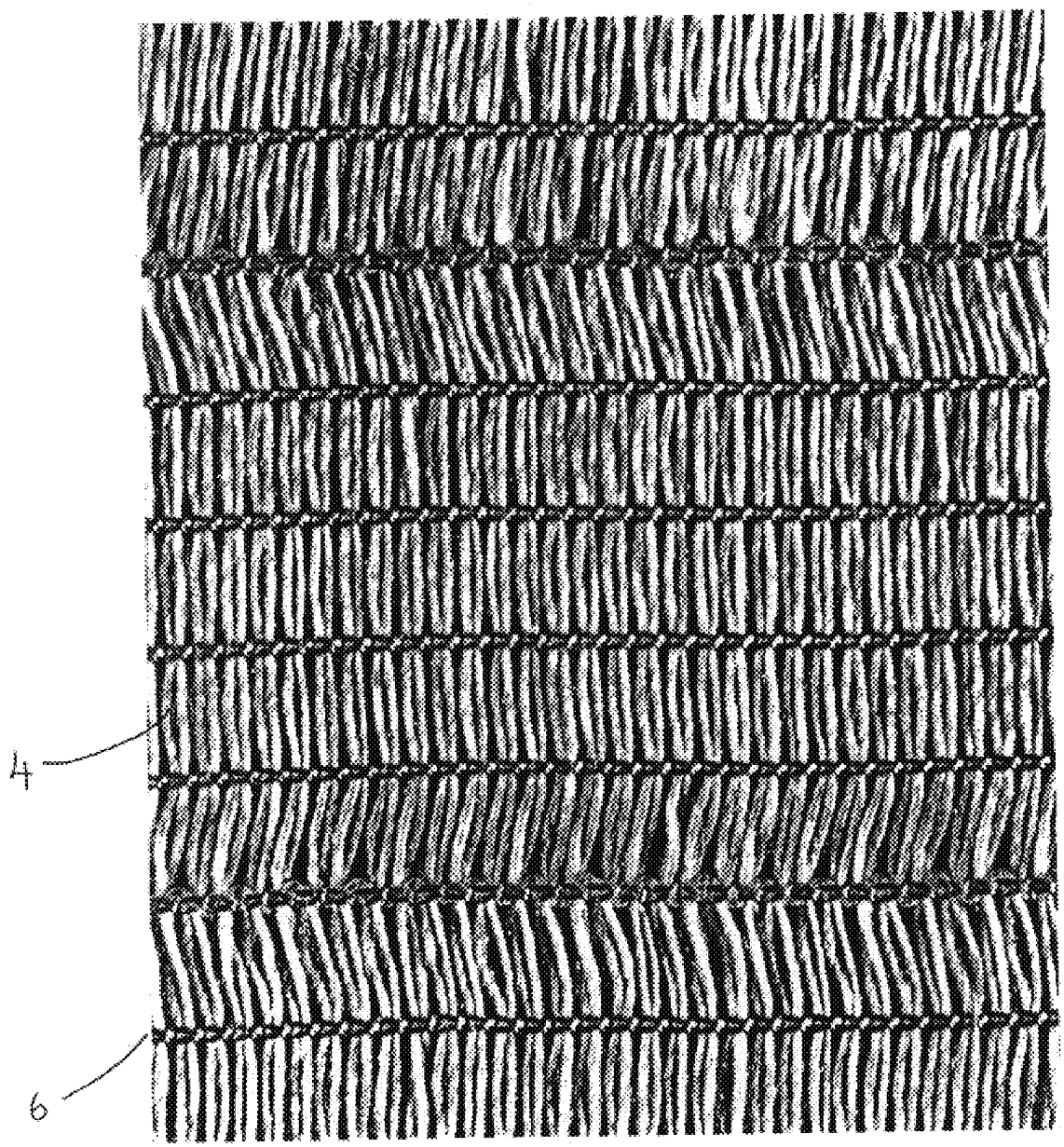
FIG. 2 is a photograph on an enlarged scale of a further embodiment of a wound dressing according to the invention.
Figure 3:
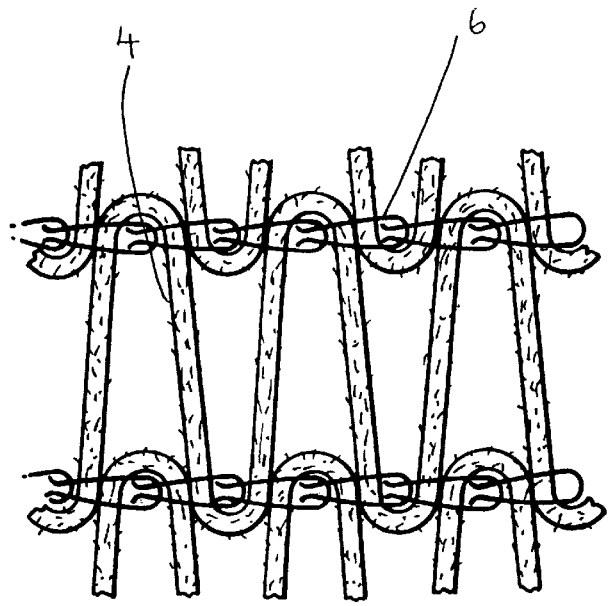
FIG. 3 is a schematic drawing showing the knitted structure of the wound dressing shown in FIG. 1.
Figure 4:
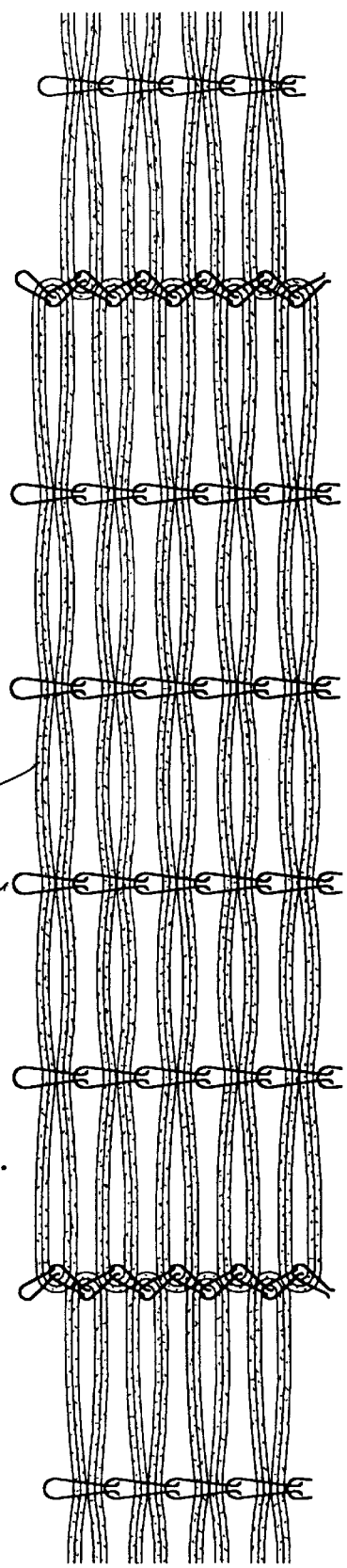
FIG. 4 is a schematic drawing showing the knitted structure of the wound dressing shown in FIG. 2.

FIG. 2 shows a similar dressing to FIG. 1 excepting that in FIG. 2 the in-laid yarn (4) is knitted as a double strand. This enables the proportion of gel-forming fibres present in the final dressing to be increased while using the same in-laid yarn. FIGS. 3 and 4 show schematically and on an enlarged scale the precise structure of preferred embodiments of the invention.

The invention is further illustrated by the following examples:

EXAMPLE 1

A wound dressing according to the invention was made as follows. A staple yarn to form the in-laid yarn of a warp knit was made from gelling fibres and textile fibres in the following way. A mixture of an alginate gelling fibre produced as described in EP-A-0721355 to Bristol-Myers Squibb Company (and as used in the product KALTOGEL ex ConvaTec) (20 kg) and polypropylene (20 kg) (all 3 denier) was cut to a staple length of 40 mm and converted into a lap of approximately 100 gsm on a conventional short staple scutching line—a Truteschler Opening line. The line comprised a feed table, coarse fibre opener, volumetric feeder, fine opener and lap former.

The lap once formed was fed into a worsted type carding machine—a Thibeau CA6 comprising a weigh pan hopper, fibre opening section and a main carding cylinder. The web of fibres formed was condensed into the form of a sliver with an average weight of 5 grammes per meter length.

The slivers were then attenuated on a conventional short-staple draw frame—a Platts Globe Draw Frame—in which rollers operated at differential surface speeds to attenuate the multiple feed of slivers (6–8) into a uniform single sliver of uniform weight and thickness (approximately 3 g per meter length).

The drawn sliver was converted into roving on a roving frame which further attenuates the sliver. Twist was inserted to add cohesion to the strand. The roving was then spun on a ring spinning machine in which further drafting took place and twist was inserted to form the final yarn.

A knitted wound dressing according to the invention was prepared comprising the staple yarn described above as the in-laid yarn and a continuous filament crimped polyester yarn as the support yarn. The dressing was knitted on a crochet knitting machine (Model STP7 ex KOHLER) each needle of which creates a chain of stitches from the support or pillar yarn. The chains are held together by the in-laid yarn. 45 pillar yarn chains were knitted from 150 denier crimped polyester yarn. These were held together by 44 rows of in-laid yarn to form a dressing.

EXAMPLE 2

The dressings as shown in FIGS. 1 and 2 were warp knitted from an in-laid yarn comprising 35% by weight of alginate fibres as sold in the product Kaltogel ex ConvaTec and 65% by weight viscose fibres ex Lenzing. The support yarn was a continuous filament viscose ex Cellatex. The dressings had the following characteristics.

|  | Dressing in FIG. 1 | Dressing in FIG. 2 |
| --- | --- | --- |
| Percentage of in-laid yarn by total weight of dressing. | 73.6 | 91.6 |
| Percentage of support yarn by total weight of dressing | 26.4 | 8.4 |
| Percentage of textile fibres by total weight of dressing | 74.2 | 67.9 |
| Percentage of gelling fibres by total weight of dressing | 25.8 | 32.1 |

EXAMPLE 3

An attempt was made to knit a wound dressing on a raschel knitting machine using a yarn comprising gel-forming fibres as the support yarn. The support yarn continually broke and the attempt was abandoned. A wound dressing according to the invention was later knitted by using a support yarn free of gel-forming fibres.

What is claimed is:

1. A wound dressing having a wound-contacting surface, which dressing comprises a mixture of textile fibers and gel-forming fibres wherein the dressing is a knitted fabric comprising support yarn running substantially parallel to said wound-contacting surface and in-laid yarn comprising gel-forming fibres, the support yarn being substantially free of gel-forming fibres.

2. A wound dressing as claimed in claim 1, wherein the dressing comprises from 5% to 95% by weight of textile fibres and from 5% to 95% by weight of gel-forming fibres.

3. A wound dressing as claimed in claim 1 wherein the in-laid yarn is a staple yarn.

4. A wound dressing as claimed in claim 1 wherein the in-laid yarn comprises from 0% to 80% by weight of textile fibre and 20% to 100% by weight of gel-forming fibre.

5. A wound dressing as claimed in claim 1 wherein the support yarn is a continuous filament viscose, polyester or polypropylene yarn.

6. A wound dressing as claimed in claim 1 wherein the fabric comprises from 5% to 80% by weight of support yarn and from 20% to 95% by weight of in-laid yarn.

7. A wound dressing as claimed in claim 1 wherein the fabric is a warp knitted fabric.

8. A wound dressing as claimed in claim 1 wherein the fabric is a Raschel knitted fabric.

9. A wound dressing as claimed in claim 1 wherein the gel forming fibres have an absorbency of at least 2 g/g.

10. A wound dressing as claimed in claim 1 wherein the gel forming fibres are hygroscopic fibres which upon the uptake of wound exudate become moist and slippery or gelatinous.

11. A wound dressing as claimed in claim 1 wherein the gel forming fibres are sodium carboxymethylcellulose fibres, chemically modified cellulosic fibres, pectin fibres, alginate fibres, fibres made from a composite of alginate and another polysaccharide, chitosan fibres, hyaluronic acid fibres, or other polysaccharide fibres or fibres derived from gums.

12. A wound dressing as claimed in claim 11 wherein the gel forming fibres are alginate or alginate composite fibres, the alginate composite fibres having an alginate content of more than 35% by weight.

13. A method for the treatment of a wound comprising placing a wound dressing of claim 1 in direct contact with the wound.

14. A wound dressing as claimed in claim 12 wherein the alginate composite fibres have an alginate content of more than 50% by weight.

* * * * *